US008401884B1

(12) United States Patent
Kinney

(10) Patent No.: US 8,401,884 B1
(45) Date of Patent: Mar. 19, 2013

(54) ELECTRONIC SCHEDULING FOR WORK SHIFTS

(75) Inventor: Lorane Kinney, Omaha, NE (US)

(73) Assignee: Avantas L.L.C.

( * ) Notice: Subject to any disclaimer, the term of this patent is extended or adjusted under 35 U.S.C. 154(b) by 1975 days.

(21) Appl. No.: 11/267,988

(22) Filed: Nov. 7, 2005

(51) Int. Cl.
*G06Q 10/00* (2012.01)
(52) U.S. Cl. .................................................. 705/7.18
(58) Field of Classification Search ............ 705/9, 7.18
See application file for complete search history.

(56) References Cited

U.S. PATENT DOCUMENTS

| | | | | |
|---|---|---|---|---|
| 5,960,411 | A * | 9/1999 | Hartman et al. ............ | 705/26 |
| 6,049,776 | A * | 4/2000 | Donnelly et al. ............ | 705/8 |
| 6,587,831 | B1 * | 7/2003 | O'Brien ....................... | 705/8 |
| 7,499,869 | B2 * | 3/2009 | Iknoian ........................ | 705/9 |
| 2002/0004742 | A1 * | 1/2002 | Willcocks et al. ........... | 705/14 |
| 2002/0103691 | A1 * | 8/2002 | Smith ........................... | 705/9 |
| 2002/0143621 | A1 * | 10/2002 | Donnelly et al. ............ | 705/14 |
| 2002/0178074 | A1 * | 11/2002 | Bloom .......................... | 705/26 |
| 2003/0220829 | A1 * | 11/2003 | Seally .......................... | 705/9 |
| 2004/0193472 | A1 * | 9/2004 | Ramakrishnan et al. .... | 705/9 |
| 2005/0054381 | A1 * | 3/2005 | Lee et al. ................. | 455/557 |
| 2005/0055303 | A1 * | 3/2005 | Routtenberg ............... | 705/37 |
| 2005/0096962 | A1 * | 5/2005 | Narasimhan et al. ........ | 705/9 |
| 2005/0137925 | A1 * | 6/2005 | Lakritz et al. ............... | 705/8 |
| 2006/0111959 | A1 * | 5/2006 | Tarr et al. .................... | 705/10 |
| 2006/0136241 | A1 * | 6/2006 | De Vries ..................... | 705/1 |
| 2006/0224477 | A1 * | 10/2006 | Garcia et al. ................ | 705/32 |
| 2007/0179830 | A1 * | 8/2007 | Iknoian ........................ | 705/9 |
| 2007/0299714 | A1 * | 12/2007 | Levine et al. ................ | 705/9 |
| 2008/0027783 | A1 * | 1/2008 | Hughes et al. ............... | 705/9 |
| 2008/0046305 | A1 * | 2/2008 | Garcia et al. ................ | 705/9 |
| 2008/0082391 | A1 * | 4/2008 | Gomez ........................ | 705/9 |
| 2008/0300954 | A1 * | 12/2008 | Cameron et al. ............ | 705/9 |
| 2008/0300955 | A1 * | 12/2008 | Hamilton et al. ........... | 705/9 |

OTHER PUBLICATIONS

Baldenius, Tim et al., Incentives for Efficient Inventory Management: The Role of Historical Cost, Jul. 2005, Management Science, vol. 51, Iss. 7; p. 1032.*

* cited by examiner

*Primary Examiner* — Andre Boyce
(74) *Attorney, Agent, or Firm* — Holland & Hart LLP

(57) ABSTRACT

A computer-implemented shift scheduling system and method are disclosed that present data to workers relating to unfilled work shifts. Selected shifts are compiled as shift data for each worker. Worker accreditation may be tracked and used to determine access to the database of unfilled work shifts. Work shift data may be grouped into categories according to an employers worker needs for specific shifts. Pay rate incentives may be associated with one or more categories and indicated on presentment of the work shift data. Remote worker access to the scheduling system may be provided in LAN or WAN environments.

17 Claims, 6 Drawing Sheets

ELECTRONIC SCHEDULING FOR WORK SHIFTS

BACKGROUND

Employers of various types and sizes employ non-routine labor for a wide range of needs. For example, many hospitals employ a core staff of nurses that work a baseline number of hours year-round. However, patient care demands do not remain constant throughout the year. Moreover, there are routine seasonal events, such as cold and flu seasons, vacation demands coinciding with school vacations, and holidays that cut into the available core workforce. Accordingly, many employers, such as hospitals, draw from pools of contingency labor to staff their business according to these variations. Other types of employers, including many from the construction and food service industries, draw solely from non-routine labor pools, scheduling workers to fill shifts as work becomes available. However, several deficiencies exist with the manner in which such non-routine labor pools are operated and utilized.

Worker demand is difficult to accurately predict. Many prior art systems and methods of staff scheduling employ one or more managers who staff certain work shifts based on their recollections of the employer's needs and deficiencies in past years. More often than not, this results in a staffing surplus or deficiency, either of which being costly to the employer. A better gauge is needed to assist in determining an employer's worker needs for particular times of the year. Moreover, the staffing of a large workforce by one or more individuals may become chaotic at times, resulting in human errors, let alone the waste of managerial resources that results from delegating the interactive scheduling task to one or more of the employer's management personnel. A self administering system, that is accessible from the employer's place of business, the worker's homes, and many places in between is crucial for creating an efficient and effective staffing solution that limits an employer's hands-on involvement.

Many prior art methods of staffing non-routine labor also fail to adequately fill staffing needs due to a lack of worker motivation. Certain shifts are less desirable to employees, due to the shift's length or the time of day in which it is scheduled. Other shifts simply occur at difficult times of the year, such as shifts that span holidays. Due to the failure of prior art staffing methods, many such shifts go under staffed. A scheduling method and system are needed that provide sufficient incentives to fill these shifts without putting a strain on the employer's staffing budget.

Staffing non-routine labor is difficult enough without having to be concerned with the accreditation of the staff being scheduled. A manual system makes tracking accreditation nearly impossible for large pools of workers, let alone for industries that require more than one type of licensure or certification for each worker on staff. Accordingly, a need exists for a system that can track the accreditation of a pool of workers as it schedules the pool for an employer and prevents the scheduling of an unqualified worker.

SUMMARY

This Summary is provided to introduce a selection of concepts in a simplified form that are further described below in the Detailed Description. This Summary is not intended to identify key features or essential features of the claimed subject matter. Moreover, this Summary is not intended for use as an aid in determining the scope of the claimed subject matter.

A computer-implemented scheduling system is provided for electronically presenting work schedule data to workers. Unfilled work shifts are created by an employer's anticipated worker needs for specific future dates. Depending on the employer's anticipated needs and other relevant factors, the unfilled work shifts may be grouped into different categories, with each pay at different rates. In one embodiment, high need shifts pay certain predetermined sums in addition to a standard base rate, whereas lower may receive little or no pay in addition to the base rate.

In one embodiment, the workers' access to the work schedule data will be limited to work shifts for which the workers are qualified, according to a predetermined accreditation threshold. In one embodiment, worker accreditation is tracked to assist in worker compliance with predetermined accreditation levels. Once the scheduling system is accessed, workers may select unfilled future shifts to work, creating shift data. The work schedule data is amended according to the workers' selections. Notices may be transmitted to the workers to confirm. Various user interfaces are provided, which present the work shift data to the workers. In one embodiment, a high need shift may be highlighted in the form of additional user interfaces. A shopping-cart method of accumulating selected shifts may be provided to assist the workers as they access the scheduling system. Pay rate incentives may also be provided to support other scheduling issues, such as early sign-up. Likewise, disincentives may be placed on workers for various reasons, such as frequent self-cancellation of selected shifts or the failure to maintain specific accreditation.

It is therefore a principal object of the present invention to provide a system and method of electronically scheduling work shifts.

A further object of the present invention is to provide a computer-implemented method of scheduling work shifts that is substantially self-administering.

Still another object of the present invention is to provide a computer-implemented shift scheduling system that is accessible by workers form remote computing devices.

Yet another object of the present invention is to provide a computer-implemented shift scheduling system that provides sufficient incentives to substantially fill high need shifts without exceeding an employer's staffing budget.

A further object of the present invention is to provide a computer-implemented method of scheduling work shifts that is sufficiently flexible to be implemented in a wide array of businesses.

Still another object of the present invention is to provide a computer-implemented shift scheduling system that tracks worker accreditation relating to the worker's duties for an employer.

Yet another object of the present invention is to provide a computer-implemented shift scheduling system that tracks and stores work schedules for a plurality of workers.

These and other objects of the present invention will be apparent upon a review of the Detailed Description and the accompanying Figures.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION

Embodiments are described more fully below with reference to the accompanying drawings, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. Accordingly, embodiments may entirely take the form of a hardware implementation, a software implementation or an implementation combining hardware and software aspects. The following detailed description is, therefore, not to be taken in a limiting sense.

Figure 1:
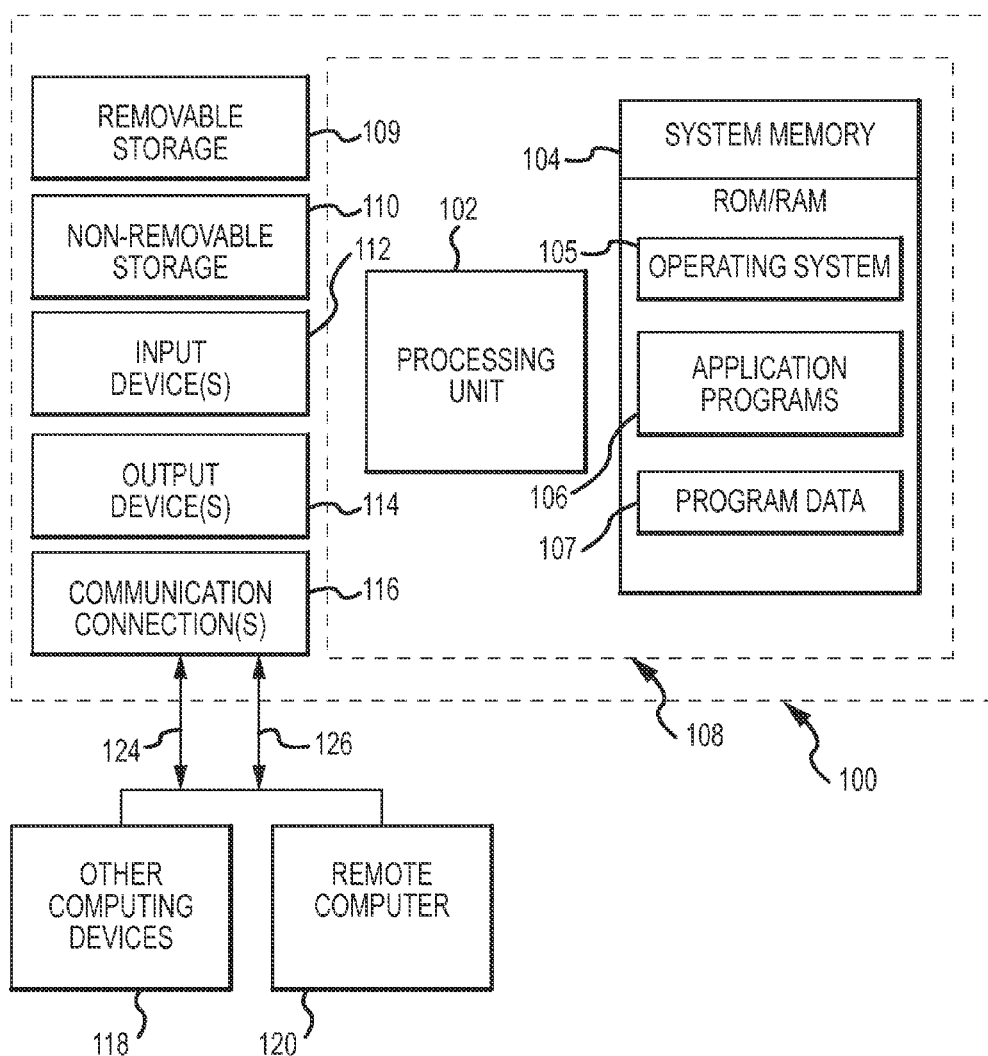
FIG. 1 is a functional block diagram of a computing system adapted to implement an embodiment of the present invention.

FIG. 1 illustrates an example of a suitable computing system environment in the form of a computing device 100 on which the present invention may be implemented. The computing device 100 is only one example of a suitable computing environment and is not intended to suggest any limitation as to the scope of use or functionality of the invention. Neither should the computing device 100 be interpreted as having any dependency or requirement relating to any one or combination of components illustrated in the exemplary operating environment. The invention is operational with numerous other general purpose or special purpose computing system environments or configurations. Examples of well known computing systems, environments, and/or configurations that may be suitable for use with the invention include, but are not limited to, personal computers, server computers, hand-held or laptop devices, network PCs, minicomputers, mainframe computers, distributed computing environments that include any of the above systems or devices, and the like.

The invention may be described in the general context of computer-executable instructions, such as program modules, being executed by a computer. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

Referring to FIG. 1, an exemplary system for implementing the invention includes a computing device, such as computing device 100. In a basic configuration, computing device 100 typically includes at least one processing unit 102 and system memory 104. Depending on the exact configuration and type of computing device, system memory 104 may be volatile (such as RAM), non-volatile (such as ROM, flash memory, and the like) or some combination of the two. System memory 104 typically includes operating system 105, one or more application programs 106, and may include program data 107. Examples of application programs 106 include phone dialer programs, e-mail programs, scheduling programs, PIM (personal information management) programs, word processing programs, spreadsheet programs, Internet browser programs, and so forth. This basic configuration is illustrated in FIG. 1 by those components within dashed line 108.

Computing device 100 may also have additional features or functionality. For example, computing device 100 may also include additional data storage devices (removable and/or non-removable) such as, for example, magnetic disks, optical disks, or tape. Such additional storage is illustrated in FIG. 1 by removable storage 109 and non-removable storage 110. Computer storage media may include volatile and non-volatile, removable and non-removable media implemented in any method or technology for storage of information, such as computer readable instructions, data structures, program modules or other data. System memory 104, removable storage 109 and non-removable storage 110 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 100. Any such computer storage media may be part of device 100. Computing device 100 may also have input device(s) 112 such as a keyboard, mouse, pen, voice input device, touch input device, etc. Output device(s) 114 such as a display, speakers, printer, etc. may also be included. All these devices are known in the art and need not be discussed at length here.

Computing device 100 also contains communication connection(s) 116 that allow the device to communicate with other computing devices 118, such as over a network or a wireless mesh network. Communication connection(s) 116 is an example of communication media. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. The term computer readable media as used herein includes both storage media and communication media.

The computing device 100 may operate in a networked environment using logical connections to one or more remote computers, such as a remote computer 120. The remote computer 120 may be a personal computer, a server, a router, a network PC, a peer device, or other common network node, and typically includes many or all of the elements described above relative to the computing device 100, although only a memory storage device 122 has been illustrated in FIG. 1. The logical connections depicted in FIG. 1 include a local area network (LAN) 124 and a wide area network (WAN) 126, but may also include other networks, such as wireless networks. Such networking environments are commonplace in offices, enterprise-wide computer networks, intranets, and the Internet. When used in a LAN networking environment, the computing device 100 is connected to the LAN 124 through a network interface or adapter. When used in a WAN networking environment, the computing device 100 typically includes an internal or external modem or other means for establishing communications over the WAN 126, such as the Internet. It will be appreciated that the network connections shown are exemplary and other means of establishing a communications link between the computers may be used.

One preferred application program 106 that may be provided assists in the creation of work schedule data, which may be stored as a portion of the program data 107. The work schedule data should be related to specific, unfilled work shifts needed by an employer. In some instances it is contemplated that the employer will know exactly the number of workers required for the business at the specific time periods in question. However, in many instances, non-routine labor may be used to supplement a core work staff or to completely staff one or more particular jobs. Accordingly, in such instances, creation of the work schedule data may require the estimation of an employer's needs. This may be accomplished using historical data of similar time frames, for similar tasks, previously scheduled by the employer. Considerations that may lower the number of available core and non-routine labor may need to be considered. These considerations may include variables, such as cold and flu seasons, frequently requested periods of vacation, that coincide with school vacation calendars, and working periods that span one or more holidays. Regardless, the needed work shifts should be compiled as work schedule data and made available to the system memory 104 of the computing device 100.

In the assembly of the work schedule data, it may be desirable to create one or more incentives and/or disincentives to ensure the highest probability that all needed work shifts will be selected and filled by one or more workers. In one embodiment, workers may be scheduled to be paid according to a uniform pay rate. However, the specific unfilled work shifts that comprise the work schedule data may be arranged into a plurality of separate categories according to the employer's anticipated worker needs at predetermined times. The separate categories of unfilled work shifts may be provided with different incentive pay rates, wherein categories having higher anticipated worker needs, such as peak business periods, holidays, etc., pay higher rates than categories having lower anticipated worker needs, such as off-season periods for the business. In the example where a uniform base pay is provided to all workers who perform substantially similar functions for the employer, the pay rate incentives may take the form of heightened pay that is broken down by the hour, the shift, a block of shifts, etc. Specific, non-limited examples of such pay incentives are discussed hereinbelow.

One or more workers should be provided access to the work schedule data so that the specific unfilled work shifts may be reviewed and selected by the workers. In one preferred embodiment, the workers are provided electronic access to the work schedule data. Depending upon the particular employer and its needs, the electronic access may be provided in a multitude of different forms. As discussed previously, the computing device 100 is provided with communication connection(s) 116 that allow the device to communicate with other computing devices 118 and/or remote computers 120. Accordingly, while a stand alone computing device 100 is contemplated, networked systems, whether in a LAN or WAN networking environment, will likely provide an employer with greater flexibility. Accordingly, intranet and Internet applications are contemplated, which provide flexible remote access to one or more workers.

Figure 2:
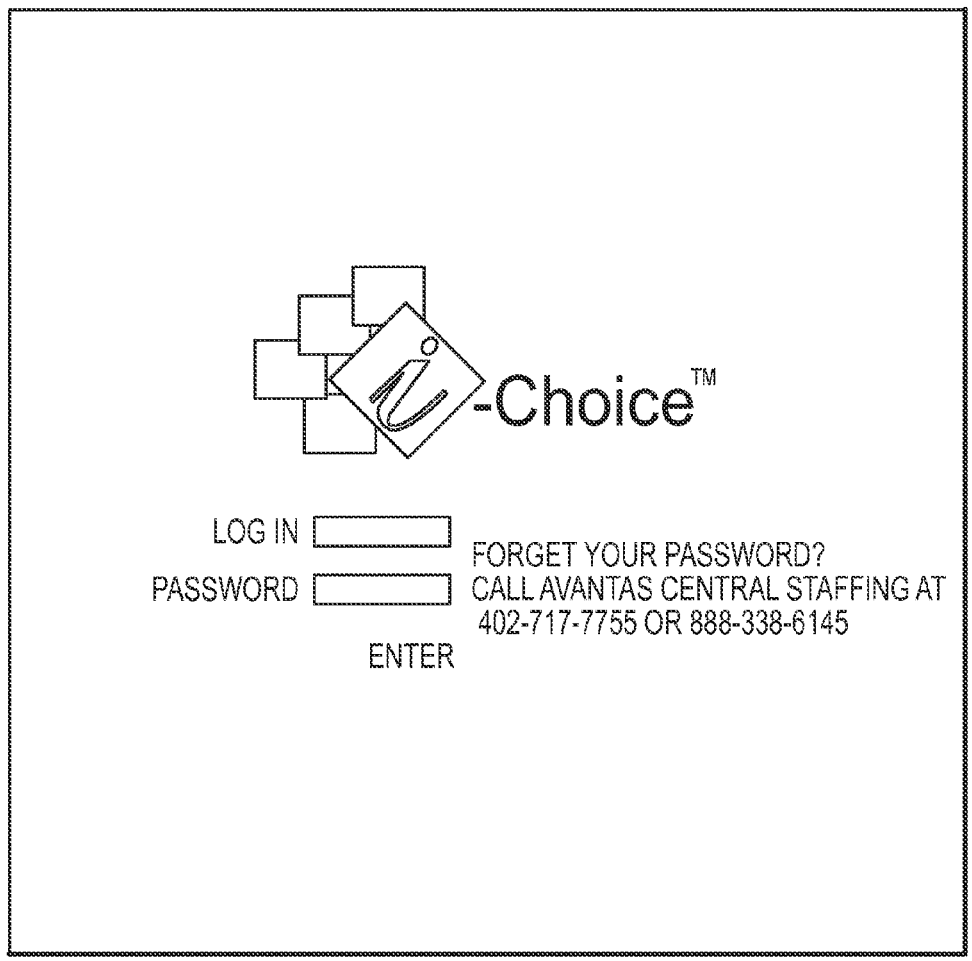
FIG. 2 depicts a screen shot of an exemplary user interface for accessing the scheduling system.

Regardless of these specific configurations of the scheduling system, FIG. 2 depicts a screen shot of an exemplary user interface for accessing the scheduling system. A login and password may be pre-assigned to select workers or an on-line sign-up may be provided. Once the system is accessed, an optional worker profile may be created.

Figure 3:
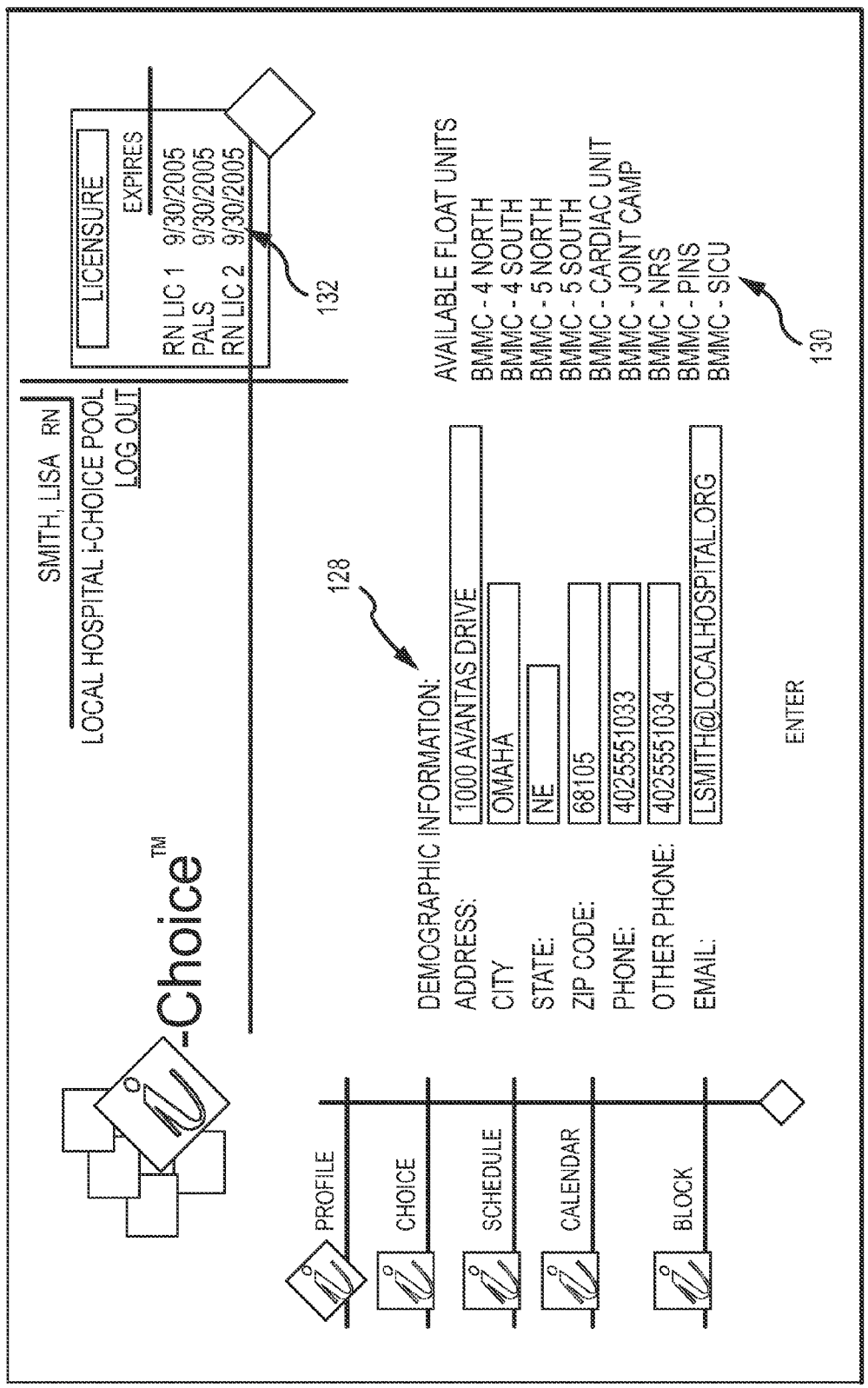
FIG. 3 depicts a screen shot of an exemplary user interface for a user profile within the scheduling system.

FIG. 3 depicts a screen shot of an exemplary user interface for a user profile for the scheduling system. Within that profile, demographic information 128 may be entered that includes basic contact information. A permissions window 130 may also be provided that identifies one or more departments, tasks, etc. for which the particular worker is authorized to work for the particular employer. An accreditation window 132 may also be provided that displays accreditation data relating to worker accreditation, such as licensure, certifications, and the like that are desirable for the worker to possess prior to working one or more of the unfilled work shifts for the employer. The accreditation window 132 may also provide a display of the expiration dates for the various accreditation data being stored so that the worker may be easily notified when it is time to renew one or more aspects of their accreditation. System tracking of a workers' accreditation is one manner in which the scheduling system may allow or deny access to one or more portions of the work schedule data. For example, if a worker does not have a particular required accreditation, certain unfilled work shifts may not be presented or otherwise made available to the worker when that worker is reviewing that work schedule data for shift selection.

Figure 4:
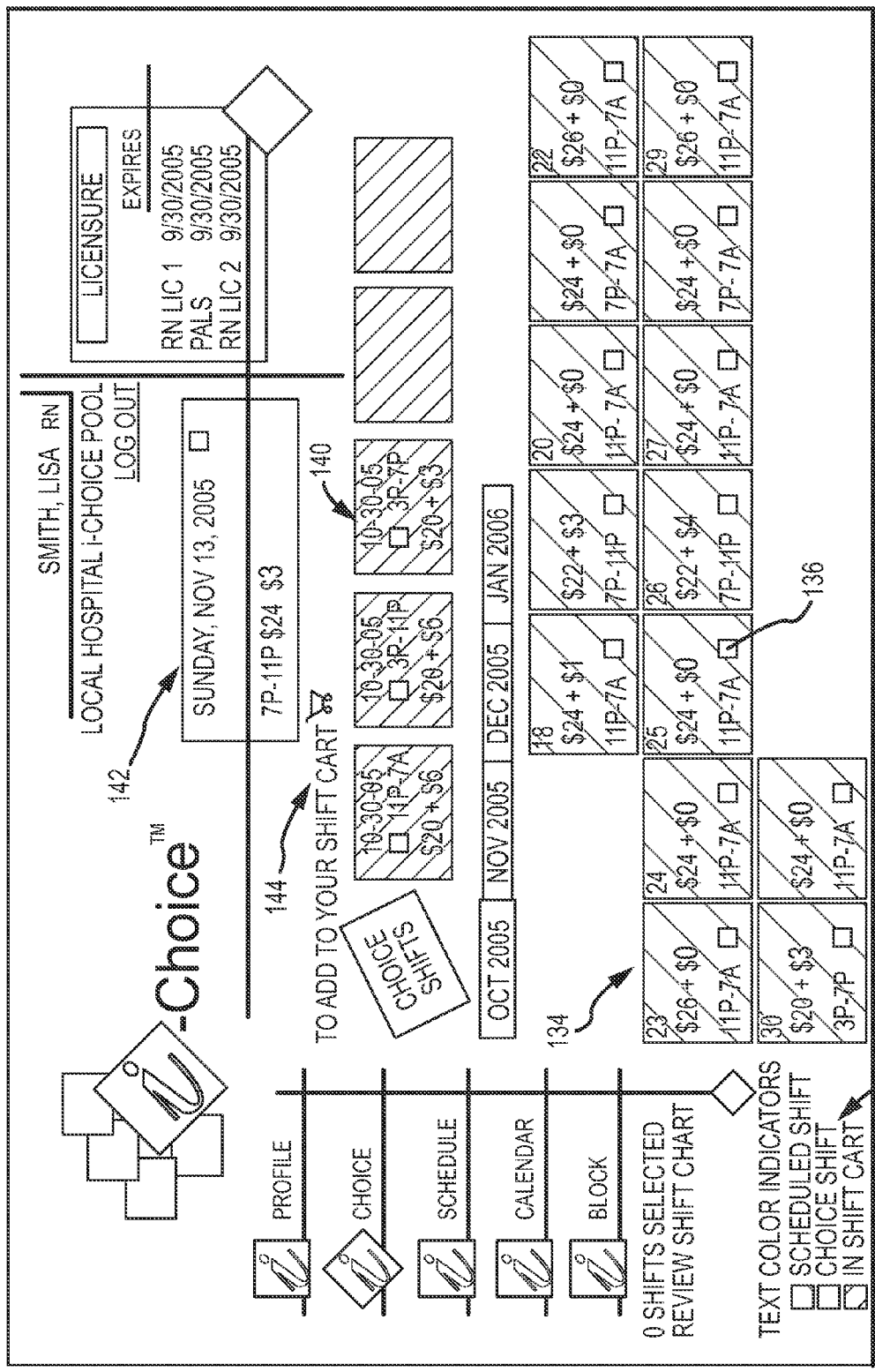
FIG. 4 depicts a screen shot of an exemplary user interface for viewing and selecting unfilled work shifts within the scheduling system.

FIG. 4 depicts a screen shot of an exemplary user interface for viewing and selecting unfilled work shifts within the scheduling system. In one embodiment, the work schedule data is presented to the worker in a calendar window 134 that may identify individual days, weeks, months, and the like. In the example depicted in FIG. 4, the different pay rates, associated with unfilled work shifts within the separate categories are indicated on the calendar window 134. Specifically, the calendar window 134 depicts available shifts for the month of October, 2005. It can be seen that a separate window is provided for October 26, which shows an available shift from 7:00 p.m. until 11:00 p.m. that pays a base rate of $22.00 per hour but includes an incentive pay rate bonus of $4.00 per hour. A graphic user interface, such as the selection box 136 or other similar GUI may be provided so that the worker may select that particular shift to work. The example also shows an October 27 shift, from 11:00 p.m. to 7:00 a.m., that pays a higher base rate of $24.00 per hour but does not include any incentive pay. It is contemplated that the calendar 134 may take many forms, according to the employer's needs. However, for those days where no shifts are made available, those days may be excluded, as shown in FIG. 4. Moreover, text color indicators, such as those depicted in the text color indicator window 138 may be provided to further distinguish between the shifts depicted on the calendar window 134, such as between selected and unfilled shifts, high need and low need shifts, and the like.

In one embodiment, unfilled work shifts having high-end anticipated worker needs may be presented on the calendar window 134 and in one or more additional displays that highlight the unfilled shifts having high-anticipated worker needs. For example, choice shift windows 140 are depicted in FIG. 4, just above the calendar window 134. Still another premier shift window 142 is depicted as being displayed above the choice shift windows 140. Graphic user interfaces similar to those used with the calendar window 134 may be provided within the choice shift windows 140 and premier shift window 142 to provide a means for allowing a worker to select the shifts presented. An optional shift cart 144 may be provided that compiles shift data relating to specific work shifts selected by the worker. A separate window may be provided for viewing the shifts selected and placed within the shift cart.

Figure 5:
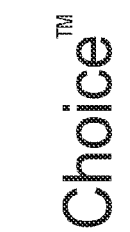
FIG. 5 depicts a screen shot of an exemplary user interface for viewing and accessing quarterly work schedule data and/or shift data.
Figure 6:
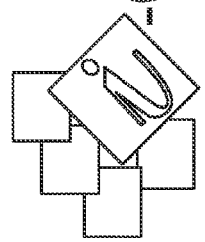
FIG. 6 depicts a screen shot of an exemplary user interface for viewing and accessing monthly work schedule data and shift data.

FIG. 5 depicts a screen shot of an exemplary user interface for viewing and accessing quarterly work schedule data and/or shift data relating to work shifts selected by the worker. It is contemplated that each of the individual days, weeks and months within the quarterly format 136 may be provided to operate in a manner similar to those identified hereinabove with respect to the calendar window 134. Likewise, FIG. 6 depicts a screen shot of an exemplary user interface for viewing and accessing monthly work scheduled data and shift data that may be selectively printed by workers for their records. Optional list views may also be provided, according to the desires of the worker.

The scheduling system may be provided to compile individual worker data sets to at least temporarily store the shift data for the individual workers. It is contemplated that individual workers may be provided access to these worker data sets to review and update the same. Available updating permissions may be provided in the form of updating accreditation information, adding selected work shifts and canceling previously selected shifts. Notices may be generated and transmitted to workers to confirm updates made by the worker to their demographic information, accreditation information, the cancellation or addition of work shifts, and the like. It is contemplated that the notices may be provided through the generation of emails, pre-recorded telephone messages or various hard copy formats delivered directly to the workers.

The flexibility and data storage capabilities of the scheduling system allow for the implementation of various incentives and disincentives to facilitate the scheduling process. For example, incentives may be provided to workers for selecting work shifts as far in advance as possible. Such incentives may include a pay rate that gradually decreases over time as unfilled work shifts remain unfilled, started on a date on which the work schedule data is created. This provides a worker with the incentive to log onto the scheduling system well in advance and select various unfilled work shifts. Similarly, where a plurality of workers are required to fill a certain work shift, pay rates may gradually decrease as workers select the individual spots that comprise a single shift. For example, a worker may be paid one or more dollars per hour as a pay rate bonus for being the first to sign up for a particular shift, whereas the last worker to sign up for that particular shift may be provided with no pay rate bonus. It is contemplated that the scheduling system will permit workers to self-cancel work shifts that the worker had previously selected. Incentives may be provided to those workers who do not routinely self-cancel such work shifts, such as preventing those workers who routinely self-cancel work shifts from accessing work scheduling data after a predetermined number of work shifts have been self-cancelled. Similarly, workers may be prevented from receiving heightened pay rates for work shifts selected by those workers, despite a heightened worker need for those shifts, if the worker has previously self-cancelled a pre-determined number of shifts.

Although the invention has been described in language that is specific to structural features and/or methodological steps, it is to be understood that the invention defined in the appended claims is not necessarily limited to the specific features or steps described. Rather, the specific features and steps are described as forms of implementing the claimed invention. Since many embodiments of the invention can be made without departing from the spirit and scope of the invention, the invention resides in the claims hereinafter appended.

What is claimed is:

1. A computer-implemented method for staffing a work schedule, the method comprising:
providing a computing device that includes a processor, a data storage medium operatively coupled with said processor that is capable of at least temporarily storing work schedule data and tit least one computer readable medium operatively coupled with said processor and said data storage medium; said at least one computer readable medium comprising software to manipulate said work schedule data; the computing device being operatively coupled with an electronic network;
creating work schedule data, wherein the work schedule data is at least partially related to specific unfilled work shifts whereby each work shift is assigned a uniform pay rate that is relative to characteristics of each such work shift, wherein the specific unfilled work shifts within said work schedule data are arranged into a plurality of separate categories according to an employer's anticipated worker needs at predetermined times, wherein said separate categories of unfilled work shifts have different pay rates, wherein categories having higher anticipated worker needs pay higher rates than categories having lower anticipated worker needs, wherein said work schedule data is presented to said at least one worker in a calendar format identifying individual days;
storing said work schedule data on said data storage medium;
at least one worker electronically accessing said work schedule data and selecting one or more work shifts to work;
creating shift data, wherein the shift data is related to specific work shifts selected by said at least one worker;
storing said shift data on said data storage medium; and
the computing device amending said work schedule data in accordance with said shift data by identifying the specific work shifts selected by the at least one worker as having been selected.

2. The computer-implemented method of claim 1 wherein said different pay rates, associated with unfilled work shifts within said separate categories, are indicated on said calendar.

3. The computer-implemented method of claim 1 wherein said shift data is presented to said at least one worker on said calendar.

4. The computer-implemented method of claim 1 wherein unfilled shifts having high-anticipated worker needs are presented on said calendar and in one or more additional displays that highlight said unfilled shifts having high anticipated worker needs.

5. The computer-implemented method of claim 1 wherein individual worker data sets are created to at least temporarily store said shift data for individual workers.

6. The computer-implemented method of claim 5 wherein workers may remotely access individual worker data sets.

7. The computer-implemented method of claim 5 wherein each of said individual worker data sets are comprised of accreditation data relating to worker accreditation that is at least desirable for a worker to possess prior to working said unfilled work shifts.

8. The computer-implemented method of claim 7 wherein the only unfilled work shifts accessible by said at least one worker are unfilled work shifts for which said at least one worker maintains a predetermined level of worker accreditation.

9. The computer-implemented method of claim 7 wherein said accreditation data is comprised of expiration dates for said worker accreditation.

10. The computer-implemented method of claim 1 wherein said work shift data is selectively presented to said at least one worker in a shopping cart format.

11. The computer-implemented method of claim 1 wherein an average pay rate for work shifts selected by said at least one worker is calculated and presented to said at least one worker.

12. The computer-implemented method of claim 1 wherein a scheduling notice is generated and transmitted to said at least one worker if specific work shifts are selected by said at least one worker.

13. The computer-implemented method of claim 1 wherein incentives are provided to said at least one worker for selecting work shifts as far in advance as possible; said incentives comprising a pay rate that gradually decreases over time as unfilled work shifts remain unfilled, starting from a date on which said work schedule data is created.

14. The computer-implemented method of claim 1 wherein incentives are provided to said at least one worker for selecting work shifts as far in advance as possible; said incentives comprising a pay rate that gradually decreases as unfilled work shifts are filled.

15. The computer-implemented method of claim 1 wherein incentives are provided to said at least one worker for selecting work shifts as far in advance as possible; said incentives comprising the cancellation of selected work shifts in a reverse order from which they were selected over time, if an employer cancels work shifts.

16. The computer-implemented method of claim 1, further comprising:
    determining a threshold number of shifts that should not be cancelled by said at least one worker; wherein incentives are provided to said at least one worker for not self-canceling work shifts selected by said at least one worker; said incentives comprise preventing said at least one worker from electronically accessing said work schedule data or selecting work shifts to work if said at least one worker self-cancels at least said threshold number of work shifts.

17. The computer-implemented method of claim 1, further comprising:
    determining a threshold number of shifts that should not be cancelled by said at least one worker; wherein incentives are provided to said at least one worker for not self-canceling work shifts selected by said at least one worker; said incentives comprise preventing said at least one worker from receiving heightened pay rates for work shifts selected by said at least one worker that have heightened worker needs if said at least one worker self-cancels at least said threshold number of work shifts.

* * * * *